United States Patent
Park et al.

(10) Patent No.: US 6,788,970 B1
(45) Date of Patent: Sep. 7, 2004

(54) SYSTEM AND METHOD FOR TREATING VASOVAGAL SYNCOPE USING CARDIAC PACING

(75) Inventors: Euljoon Park, Stevenson Ranch, CA (US); Alan H. Kadish, Skokie, IL (US); Eric Falkenberg, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 276 days.

(21) Appl. No.: 10/132,044

(22) Filed: Apr. 24, 2002

Related U.S. Application Data (63) Continuation-in-part of application No. 09/543,832, filed on Apr. 5, 2000.

(51) Int. Cl.$^7$ ............................................. A61B 1/365
(52) U.S. Cl. ..................................................... 607/17
(58) Field of Search ........................... 607/9, 14, 17–25

(56) References Cited

U.S. PATENT DOCUMENTS

| | | | | |
|---|---|---|---|---|
| 4,485,813 A | | 12/1984 | Anderson et al. ............ 128/675 |
| 4,527,568 A | | 7/1985 | Rickards ................. 128/419 PG |
| 4,535,774 A | | 8/1985 | Olson .................... 128/419 PG |
| 4,719,921 A | | 1/1988 | Chirife .................. 128/419 PG |
| 4,733,667 A | | 3/1988 | Olive et al. ............ 128/419 PG |
| 4,759,366 A | | 7/1988 | Callaghan .............. 128/419 PG |
| 4,884,576 A | | 12/1989 | Alt ...................... 128/419 PG |
| 5,139,020 A | | 8/1992 | Koestner et al. ........ 128/419 PG |
| 5,466,254 A | | 11/1995 | Helland ........................ 607/123 |
| 5,476,483 A | | 12/1995 | Bornzin et al. ................ 607/17 |
| 5,480,412 A | | 1/1996 | Mouchawar et al. ............ 607/6 |
| 5,800,467 A | | 9/1998 | Park et al. ..................... 607/17 |
| 5,919,210 A | * | 7/1999 | Lurie et al. ..................... 607/3 |
| 6,044,299 A | | 3/2000 | Nilsson ......................... 607/19 |
| 6,049,735 A | * | 4/2000 | Hartley et al. ................. 607/9 |
| 6,078,834 A | * | 6/2000 | Lurie et al. ..................... 607/3 |
| 6,208,900 B1 | | 3/2001 | Ecker et al. .................. 607/17 |
| 2002/0004670 A1 | | 1/2002 | Florio et al. .................... 607/9 |
| 2002/0004672 A1 | | 1/2002 | Florio et al. .................... 607/9 |

FOREIGN PATENT DOCUMENTS

| | | | |
|---|---|---|---|
| EP | 1142608 A2 | 1/2001 | .......... A61N/1/368 |

OTHER PUBLICATIONS

Barold, S. Serge et al., Recent Advances in Cardiac Pacing: Goals for the 21$^{st}$ Century, 92–95, Futura Publishing Company (1997).

Benditt; David G. et al., "Cardiac Pacing for Prevention of Recurrent Vasovagal Syncope," 204–209, Ann Intern Med. vol. 122, No. 3 (1995).

Deharo, J.C. et al., "Treatment of Malignant Primary Basodepressive Neurocardiogenic Syncope with a Rate Responsive Pacemaker Driven by Heart Contractility," 2688–2690, PACE vol. 21 (1998).

* cited by examiner

*Primary Examiner*—Jeffrey R. Jastrzab (57) ABSTRACT

A pacemaker or other cardiac stimulation device is configured to predict the onset of vasovagal syncope and administers pacing therapy to prevent the syncope from occurring. Prediction of the onset of vasovagal syncope is based upon an analysis of the contractility of the heart muscle. In an example described herein, the contractility of the heart muscle is detected and compared with the average contractility. If the current contractility exceeds the average contractility by a predetermined threshold, a high risk of vasovagal syncope is thereby detected and the heart is paced at a vasovagal syncope prevention rate which may be, for example, 20 to 40 beats per minute faster than a previous heart rate. The contractility of the heart is determined, for example, by measuring the impedance of the heart tissue, by measuring the movement of heart tissue in the wall of the heart, by pressure using an accelerometer, or based on an electrogram signal. The contractility is averaged over a period of time to determine the average contractility.

50 Claims, 4 Drawing Sheets

SYSTEM AND METHOD FOR TREATING VASOVAGAL SYNCOPE USING CARDIAC PACING

CROSS-REFERENCE TO RELATED APPLICATIONS

This application is a continuation-in-part of copending U.S. patent application Ser. No. 09/543,832, filed Apr. 5, 2000, titled "System and Method for Prevention of Recurrent Vasovagal Syncope Using Cardiac Pacing."

FIELD OF THE INVENTION

The invention generally relates to cardiac pacing techniques and in particular to techniques for treating vasovagal syncope using cardiac pacing.

BACKGROUND OF THE INVENTION

Syncope is a sudden loss of strength or consciousness caused by reduced cerebral circulation, itself typically the result of vasodilation. Vasovagal syncope is a type of syncope referred to as a neurocardiogenic syncope wherein the syncope is triggered by an interaction between the heart and nerve tissue connected to the heart. Neurocardiogenic syncope may also be referred to as neuromediated syncope, neurally mediated syncope, neurocardiogenic syncope, cardioneurogenic syncope, vasodepressor syncope, malignant vasovagal syndrome, neurally mediated hypotension/bradycardia and cardiovascular neurogenic syncope. For vasovagal syncope, the interaction occurs between the heart and the vagus nerve.

Evidence suggests that vasovagal syncope is initially triggered by a sudden reduction in peripheral vascular resistance, perhaps resulting from stress, pooling of blood in the extremities, or other factors. As a result of the reduction in peripheral vascular resistance, the pressure of blood entering the heart drops and the amount of blood filling the ventricles prior to ventricular contractions therefore also drops. With less blood in the ventricles, the ventricles thereby contract much more quickly and vigorously than would otherwise occur in an effort to maintain a constant stroke volume. The more vigorous ventricular contractions have the effect of stimulating ventricular mechanoreceptors, also known as C fibers, that normally only respond to ventricular expansion or stretching, rather than contraction. The activation of the ventricular mechanoreceptors results in a surge in neural traffic to the brainstem, particularly to the nucleus tractus solitaries, via the vasovagal nerve.

For most people, the neurological system properly interprets the increase of activity of the mechanoreceptors as being in response to a drop in peripheral vascular resistance and compensates by increasing the heart rate and constricting the blood vessels. However, in certain patients, as a result of a neurological condition within the vagus nerve or for some other reason, the surge in neural traffic is falsely perceived by the neurological system as being representative of hypertension. In response thereto, the brainstem triggers an increase in peripheral vasodilation and a reduction in heart rate. The vasodilation and the drop in heart rate, in turn, cause a still further reduction in blood pressure, i.e., hypotension. In other words, the actions taken by the brainstem exacerbate the problem. If the degree of hypotension is sufficiently severe, cerebral hypoperfusion occurs wherein brain cells do not receive enough oxygen and, consequently, the victim loses consciousness. Accordingly, within these patients, any sudden drop in peripheral vascular resistance can trigger vasovagal syncope and the patients then suffer from recurrent vasovagal syncope. Further information regarding vasovagal syncope may be found in S. Serge Barold and Jacques Mugica, *Recent Advances in Cardiac Pacing*, Futura Publishing Company, 92–95, 1997.

As can be appreciated, loss of consciousness can be particularly dangerous for the patient if occurring while the patient is driving a motor vehicle, climbing a flight of stairs or engaged in any other activity wherein the loss of consciousness could result in injury or death. Accordingly, it is highly desirable to provide techniques for preventing or at least mitigating the symptoms that occur from vasovagal syncope or other forms of neurocardiological syncope.

One possible technique for preventing vasovagal syncope is to employ a pacemaker, or other implantable cardiac pacing device, to pace the heart to prevent the reduction in blood pressure associated with vasovagal syncope from occurring. Indeed, the American College of Cardiology-American Heart Association suggested in 1991 that vasovagal syncope in patients should be used as a Class 2 indication for pacing therapy. However, conventional cardiac pacemakers have had only limited success in preventing recurrent vasovagal syncope. (See David G. Benditt et al., *Cardiac Pacing for Prevention of Recurrent Vasovagal Syncope*, Ann Intem Med. 1995; 122; 204–209.) Insofar as vasovagal syncope is concerned, conventional pacemakers only respond to the reduction in heart rate associated therewith. The reduction in heart rate, also referred to as bradycardia, is detected by the pacemaker, which increases the heart rate to compensate. Depending upon the programming of the pacemaker, it may take five to eight seconds or more before the pacemaker begins increasing the heart rate in response to detection of bradycardia. For many patients subject to recurrent vasovagal syncope, a significant drop in blood pressure occurs before there is any bradycardia. Hence, by the time the pacemaker begins to increase the heart rate, the blood pressure will already have dropped to the point where the increase in heart rate is ineffective. In this regard, the drop in blood pressure results in significantly less blood filling the ventricles, such that there is simply not enough incoming blood to pump. Hence, overall blood pressure is not significantly increased merely by pumping the heart faster, and the aforementioned cerebral hypoperfusion still occurs resulting in unconsciousness. Moreover, for at least some patients subject to recurrent vasovagal syncope, there is no significant drop in heart rate, only a drop in blood pressure. Hence, pacemakers programmed to prevent vasovagal syncope based solely upon detection of bradycardia will have little or no effect.

Thus, bradycardia-triggered vasovagal syncope prevention techniques employed by some conventional cardiac pacemakers often fail to prevent the syncope. Moreover, conventional cardiac pacemakers are often unable to distinguish physiologic bradycardia such as that associated with sleep from bradycardia associated with vasovagal syncope or other neurocardiogenic syncope.

Accordingly, it would be highly desirable to provide improved cardiac pacing devices capable of predicting the onset of vasovagal syncope or other types of neurocardiogenic syncope, and for reliably administering pacing therapy to prevent the syncope from occurring. It is to these ends that the invention is primarily directed.

SUMMARY OF THE INVENTION

In accordance with one aspect of the invention, a cardiac pacing device is provided with a control system that is programmed or configured to execute vasovagal syncope prediction, compensation, and/or prevention algorithms for predicting the onset of vasovagal syncope and for administering pacing therapy to prevent the syncope from occurring or at least mitigate symptoms related to vasovagal syncope. That is, an increase in pacing rate can be used to compensate for the decrease in cardiac output associated vasovagal syncope that occur with pathological changes in vagal tone. Prediction of the onset of vasovagal syncope is based upon an analysis of the contractility of the heart muscle.

In an exemplary embodiment, prediction of the onset of vasovagal syncope is achieved by sensing the contractility of the heart muscle and determining whether the sensed contractility exceeds an average contractility by a predetermined threshold amount. If so, the heart is paced at a "vasovagal syncope prevention rate", which may be, for example, 20 to 40 beats per minute faster than a previous heart rate. Hereinafter, the term "vasovagal syncope prevention rate" is understood to mean a rate that prevents or mitigates the symptoms related to vasovagal syncope. The term "preventative pacing", as used herein, is also understood to include preventing or compensating for an episode of vasovagal syncope, including episodes of sudden rate drop and vasodilation that result in poor or sudden decreases in vagal tone, which are compensated by increasing cardiac output with an increase in pacing rate.

In one embodiment, the contractility of the heart is determined, for example, by measuring the electrical impedance change or pressure change in the ventricle, or by measuring the movement of heart tissue in the wall of the heart using an accelerometer. The contractility measured is averaged over a period of time to determine the average contractility.

It is recognized that the contractility of the heart may be determined in a variety of ways, as will be shown below. Since the exact method is not critical to practicing the invention, it is within the spirit of the invention that any method of determining contractility may be employed. However, for convenience and simplicity, it is preferred to employ a technique that does not require a special lead, for example, by measuring the electrical impedance or the rate of change of impedance, ventricular gradient or post-depolarization integral, QT interval, heart sounds, etc. Specially-made leads that incorporate sensors, of course, may also be used, for example, leads that measure pressure change in the ventricle, or by measuring the movement of heart tissue in the wall of the heart using an accelerometer. In any case, the contractility measured is averaged over a period of time to determine the average contractility.

In this manner, the onset of vasovagal syncope is predicted based upon changes in heart muscle contractility and syncope is substantially prevented from occurring, or at least the symptoms are mitigated, by immediately administering vasovagal syncope preventative pacing measures. Because prediction of imminent vasovagal syncope is based upon a measurement of the contractility of the heart tissue, rather than upon detection of an episode of bradycardia, vasovagal syncope is thereby detected even in circumstances wherein hypotension occurs before bradycardia or wherein bradycardia does not occur at all. Also, physiologic episodes of bradycardia, such as those associated with sleep, do not erroneously trigger the vasovagal syncope pacing therapy. Moreover, the increase in contractility associated with vasovagal syncope can be detected quickly whereas reliable bradycardia detection may require analysis of several heart beats. Hence, preventative pacing may be administered before the blood pressure has dropped significantly, as could otherwise occur if relying solely on bradycardia detection. Two or more independent contractility sensors may be provided to help prevent a false positive detection of vasovagal syncope.

Method embodiments of the invention are also provided. Other features, advantages and aspects of the invention are either described below or will be apparent from the descriptions below in combination with the accompanying drawings.

BRIEF DESCRIPTION OF THE DRAWINGS

Further features and advantages of the invention may be more readily understood by reference to the following description taken in conjunction with the accompanying drawings, in which.

DETAILED DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
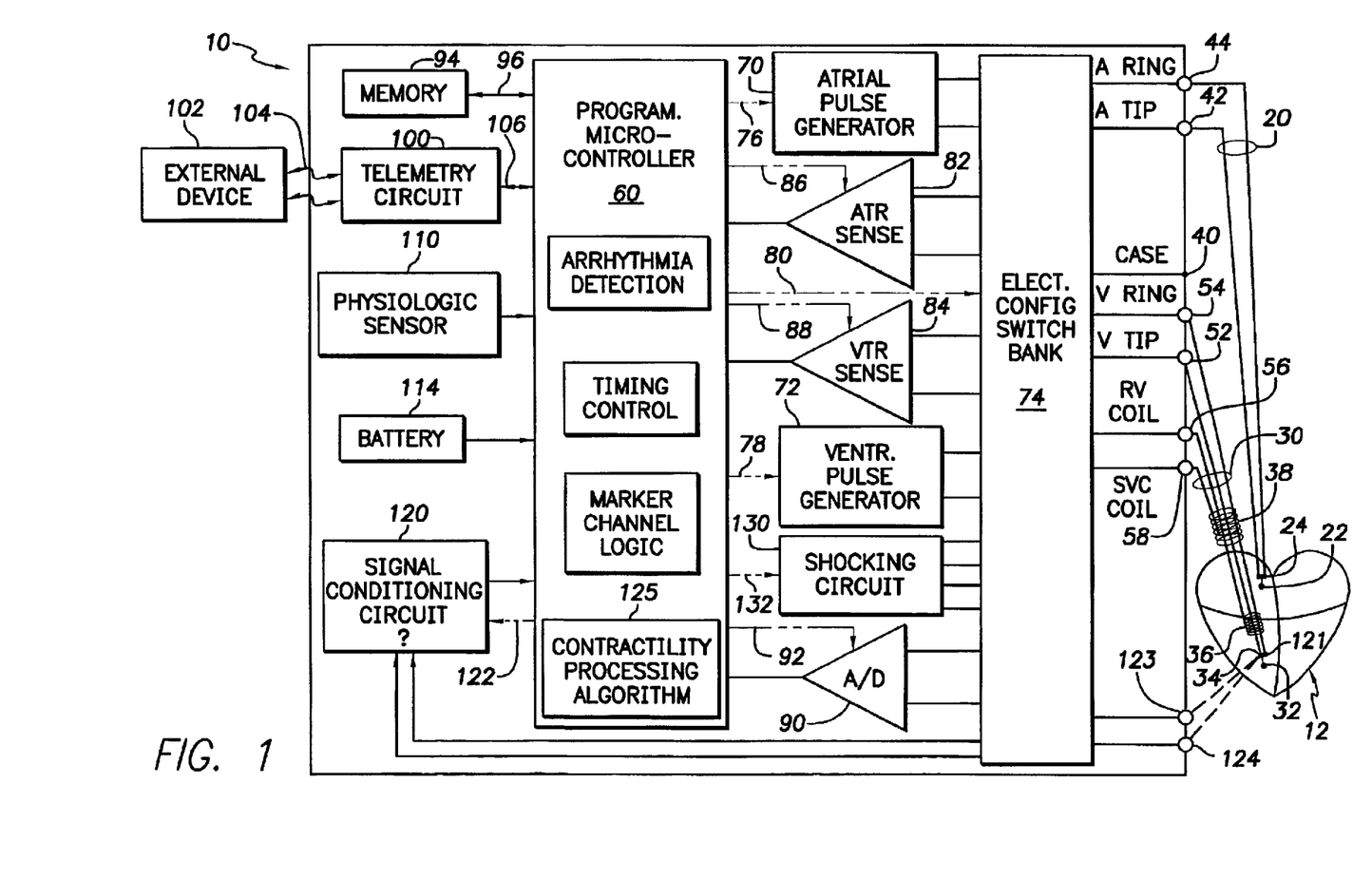
FIG. 1 is a functional block diagram of a dual-chamber implantable stimulation device illustrating the basic elements of a stimulation device which can provide cardioversion, defibrillation and pacing stimulation and can predict and prevent vasovagal syncope in accordance with an exemplary embodiment of the invention.

In FIG. 1, a simplified block diagram is shown of a dual-chamber implantable stimulation device 10 which is capable of treating both fast and slow arrhythmias with stimulation therapy, including cardioversion, defibrillation, and pacing stimulation. While a dual-chamber device is shown, this is for illustration purposes only, and one of skill in the art could readily eliminate, add or disable the appropriate circuitry to provide a single-chamber or a four-chamber stimulation device capable of treating one chamber with cardioversion, defibrillation and pacing stimulation. For a complete description of an implantable stimulation device capable of pacing and sensing in up to four chambers of the heart arid/or providing shock therapy, see U.S. application Ser. No. 09/930,725, entitled "Multi-site cardiac stimulation device for controlling Interchamber Delay" (Richard Lu) filed Aug. 14, 2001, which application is incorporated herein by reference.

To provide atrial chamber pacing stimulation and sensing, the stimulation device 10 is shown in electrical communication with a patient's heart 12 by way of an implantable atrial lead 20 having an atrial tip electrode 22 and an atrial ring electrode 24 which typically is implanted in the patient's atrial appendage.

The stimulation device 10 is also shown in electrical communication with the patient's heart 12 by way of an implantable ventricular lead 30 having, in this embodiment, a ventricular tip electrode 32, a ventricular ring electrode 34, a right ventricular (RV) coil electrode 36, and an SVC coil electrode 38. Typically, the ventricular lead 30 is transvenously inserted into the heart 12 so as to place the RV coil electrode 36 in the right ventricular apex, and the SVC coil electrode 38 in the superior vena cava. Accordingly, the ventricular lead 30 is capable of receiving cardiac signals, and delivering stimulation in the form of pacing and shock therapy to the right ventricle.

While only two leads are shown in FIG. 1, it is to be understood that additional stimulation leads (with one or more pacing, sensing and/or shocking electrodes) may be used in order to efficiently and effectively provide pacing stimulation to the left side of the heart or atrial cardioversion and/or defibrillation. For example, a lead designed for placement in the coronary sinus region could be implanted to deliver left atrial pacing, atrial shocking therapy, and/or for left ventricular pacing stimulation. For a complete description of a coronary sinus lead, see U.S. patent application Ser. No. 09/457,277, filed Dec. 8, 1999, which is a continuation-in-part of U.S. patent application Ser. No. 09/196,898, "A Self-Anchoring Coronary Sinus Lead" (Pianca et al.), filed Nov. 20, 1998 (abandoned); and U.S. Pat. No. 5,466,254, "Coronary Sinus Lead with Atrial Sensing Capability" (Helland), which patents are hereby incorporated herein by reference.

The housing 40 (shown schematically) for the stimulation device 10 includes a connector (not shown) having an atrial pin terminal 42 and an atrial ring terminal 44, which are adapted for connection to the atrial tip electrode 22 and the atrial ring electrode 24, respectively. The housing 40 further includes a ventricular pin terminal 52, a ventricular ring terminal 54, a ventricular shocking terminal 56, and an SVC shocking terminal 58, which are adapted for connection to the ventricular tip electrode 32, the ventricular ring electrode 34, the RV coil electrode 36, and the SVC coil electrode 38, respectively. The housing 40 (often referred to as the "can", "case" or "case electrode") may be programmably selected to act as the return electrode, or anode, alone or in combination with one of the coil electrodes, 36 and 38. For convenience, the names of the electrodes are shown next to the terminals.

At the core of the stimulation device 10 is a programmable microcontroller 60 which controls the various modes of stimulation therapy. As is well known in the art, the microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art as shown in FIG. 1, an atrial pulse generator 70 and a ventricular pulse generator 72 generate pacing stimulation pulses for delivery by the atrial lead 20 and the ventricular lead 30, respectively, via a switch bank 74. The pulse generators, 70 and 72, are controlled by the microcontroller 60 via appropriate control signals, 76 and 78, respectively, to trigger or inhibit the simulation pulses. The microcontroller 60 further includes timing circuitry that controls the operation of the stimulation device timing of such stimulation pulses that is well known in the art.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar or bipolar) by selectively closing the appropriate combination of switches (not shown) as is known in the art. An atrial sense amplifier 82 and a ventricular sense amplifier 84 are also coupled to the atrial and ventricular leads 20 and 30, respectively, through the switch bank 74 for detecting the presence of cardiac activity. The switch bank 74 determines the "sensing polarity" of the cardiac signal by selectively closing the appropriate switches, as is also known in the art. In this way, the clinician may program the sensing polarity independent of the stimulation polarity.

Each sense amplifier, 82 and 84, preferably employs a low power, precision amplifier with programmable gain and/or automatic gain control, bandpass filtering, and a threshold detection circuit, known in the art, to selectively sense the cardiac signal of interest. The automatic gain control enables the device 10 to deal effectively with the difficult problem of sensing the low frequency, low amplitude signal characteristics of ventricular fibrillation.

The outputs of the atrial and ventricular sense amplifiers, 82 and 84, are connected to the microcontroller 60, which, in turn, inhibit the atrial and ventricular pulse generators, 70 and 72, respectively, in a demand fashion whenever cardiac activity is sensed in the respective chambers.

For arrhythmia detection, the present device utilizes the atrial and ventricular sense amplifiers, 82 and 84, to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between sensed events (e.g., the P-P and R-R intervals) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, also known as "tiered therapy").

Cardiac signals are also applied to the inputs of an analog to digital (AID) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the atrial and ventricular leads, 20 and 30, through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patent. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 28 within each respective tier of therapy.

Advantageously, the operating parameters of the implantable device 10 may be non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through the established communication link 104.

In the preferred embodiment, the stimulation device 10 further includes a physiologic sensor 110. Such sensors are commonly called "rate-responsive" sensors. The physiological sensor 110 is used to detect the exercise state of the patient, to which the microcontroller 60 responds by adjusting the rate and AV Delay at which the atrial and ventricular pulse generators, 70 and 72, generate stimulation pulses. The type of sensor used is not critical to the present invention and is shown only for completeness.

The stimulation device additionally includes a battery 114 which provides operating power to all of the circuits shown in FIG. 1. For the stimulation device 10, which employs shocking therapy, the battery must be capable of operating at low current drains for long periods of time, and then be capable of providing high-current pulses (for capacitor charging) when the patient requires a shock pulse. The battery 114 must also have a predictable discharge characteristic so that elective replacement time can be detected. Accordingly, the device employs lithium/silver vanadium oxide batteries, as is true for most (if not all) such devices to date.

It is the primary function of the invention to function as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 130 by way of a control signal 132. The shocking circuit 130 generates shocking pulses of low (up to 0.5 Joules), moderate (0.5–10 Joules), or high energy (11 to 40 Joules), as controlled by the microcontroller 60. Such shocking pulses are applied to the patient's heart through at least two shocking electrodes, and as shown in this embodiment, using the RV and SVC coil electrodes, 36 and 38, respectively. In alternative embodiments, the housing 40 may act as an active electrode in combination with the RV electrode 36 alone, or as part of a split electrical vector using the SVC coil electrode 38 (i.e., using the RV electrode as common).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asychronously (since R-waves may be too disorganized), and pertaining exclusively to the treatment of fibrillation. Accordingly, the microcontroller 60 is capable of controlling the synchronous or asynchronous delivery of the shocking pulses.

The present invention utilizes a desired "inotropic sensor" that provides or corresponds to a measure of the instantaneous contractility of the patient's heart.

In one embodiment, the ventricular lead 30 includes at least one contractility sensor 121, e.g., an accelerometer, a pressure sensor, and/or an impedance sensor (hereinafter referred to as the "contractility sensor(s) 121").

Device 10 is configured to sense the contractility of the heart using the contractility sensor(s) 121 on ventricular lead 20 and, in response to a sudden increase in the contractility of the heart, to immediately pace the heart at an elevated rate to prevent vasovagal syncope from occurring, or to delay the progression of vasovagal syncope. To this end, device 10 includes signal conditioning circuitry 120 or other input circuit which receives analog signals via one or more terminals 123 and 124 from the contractility sensor(s) (shown schematically in dotted lines) and converts the analog sign into digital signals from processing by controller 60.

The controller 60 includes software for analyzing the signals received from the signal conditioning circuitry 120 to determine the contractility of the heart.

For example, in one embodiment, the controller 60 analyzes the signals to first estimate the amount of blood within the right ventricle. Based upon the estimate of the amount of blood in the right ventricle, controller 60 further then estimates the contractility of the muscles of the right ventricle.

The controller also determines the average contractility and stores it in memory 94 or within a separate contractility storage register (not shown). Controller 60 then compares the sensed contractility of the heart with the average contractility of the heart and controls atrial and ventricular pulse generators 70 and 72 to administer pacing pulses to the heart at an accelerated rate in an effort to compensate for the reduction in blood pressure otherwise occurring prior to vasovagal syncope.

In another embodiment, the data acquisition system 90 may acquire the intracardiac electrogram through the pacing/sensing electrodes (e.g., ventricular electrodes 32, 34 and/or atrial electrode 22, 24) or by a sensor in the housing itself, so that the signal conditioning circuit 120 can determine the patients current contractility based on, for example, the ventricular gradient, impedance, heart sounds, PEP, etc. Hereinafter the "inotropic" or "contractility" sensor, whether using a sensor on the lead (illustrated at element 121, e.g., a sensor near the ring electrode), the intracardiac electrogram, or a sensor in the housing, shall be referred to herein generally as the "contractility sensor(s) 121", since at least one, and/or more than one can be used. The processing of the contractility sensor may occur in hardware using the signal conditioning circuit 120, or using the A/D data acquisition system 90 and software in the microcontroller 60, such as, a contractility processing algorithm 125.

As noted, controller 60 may determine contractility based on pressure, acceleration or pressure signals, or a combination thereof, received from the contractility sensor(s).

Other "inotropic" sensors that can measure contractility are numerous and well known in the art.

For example, contractility may be measured using pressure waves, for example, in U.S. Pat. No. 6,208,900 (Ecker et al.) and U.S. Pat. No. 4,485,813 (Anderson et al.), which patents are hereby incorporated herein by reference.

Heart sound waves can be used to determine contractility and other related parameters (e.g., stroke volume, blood pressure and dP/dt), as disclosed in U.S. Pat. No. 6,044,299 (Nilsson), which is hereby incorporated herein by reference.

Intracardiac electrogram signals may also be basis for determining contractility, e.g., using the intracardiac electrogram to derive a "ventricular gradient" and QT interval.

"Ventricular gradient", also sometimes referred to as "paced depolarization integral", is the integral of the paced R-wave (or P-wave) signal and is also believed to correlate to contraction force. See, for example, U.S. Pat. No. 4,759,366 (Callaghan). It is further believed that the atrial contractility may be used to enhance or augment the vasovagal algorithm. The QT interval, that is the interval between a delivered ventricular stimulus and an evoked T-wave, is also based entirely on the detection of the evoked cardiac signal, as disclosed in U.S. Pat. No. 4,527,568. Both the '366 and the '568 patents are hereby incorporated herein by reference.

Combination of sensors may also be employed. For example, pre-ejection period (PEP), as taught in U.S. Pat. No. 4,719,921 (Chirife), is the sensing of the elapsed time from the ventricular depolarization corresponding to the QRS complex and the onset of ventricular ejection, which can be measured using the electrogram signal and a blood flow sensor, impedance sensor, or a ventricular volume detector, etc. The '921 patent is also hereby incorporated herein by reference.

Impedance measurements of blood in the heart have also been employed to derive contractility of the myocardium, and stroke volume in U.S. Pat. No. 4,884,576 (Alt) and U.S. Pat. No. 4,535,774 (Olsen). Also, the rate of change in impedance (dZ/dt) has been shown to correspond to contractility, see, for example, U.S. Pat. No. 4,733,667 (Olive et al.) and U.S. Pat. No. 5,800,467 (Park et al.), the disclosures of which are hereby expressly incorporated herein by reference.

For example, one technique for estimating contractility based upon electrical impedance detected within the heart is described within U.S. Pat. No. 5,800,467 to Park et al., entitled "Cardio-Synchronous Impedance Measurement System for an Implantable Stimulation Device," which is incorporated by reference herein. Briefly, blood is an electrical conductor and, hence, a decrease in the amount of blood in the ventricle results in an increase in electrical impedance. Impedance therefore, as measured within the ventricle of the heart, provides an indication of the amount of blood in the ventricle. Controller 60 monitors the impedance of the heart and detects any sharp increase in the impedance from one cycle to the next. The increase in impedance is therefore interpreted as a decrease in the amount of blood filling the ventricle during the cardiac cycle. As noted above, a sudden drop in ventricular filling causes the ventricle to contract more vigorously, i.e. the contractility of the ventricle increases. The sharp increase in contractility causes mechano-receptors within the ventricle to transmit signals to the vagus nerve, which are forwarded to the brainstem. For patients with recurrent vasovagal syncope, the resulting surge in signals is misinterpreted as being representative of hypertension and the brainstem dilates blood vessels and decreases the heart rate in an attempt to compensate for the hypertension. This results in a significant drop in blood pressure causing hypoperfusion of the cerebrum and possibly loss of consciousness. Hence, a sharp increase in impedance from one period of ventricular contraction to the next is a good indicator of the potential onset of vasovagal syncope, at least within patients who suffer from recurrent vasovagal syncope. Accordingly, the '576, '774, '667 and '467 patents are all hereby incorporated herein by reference.

Cardiac wall motion sensors enable the use of cardiac wall acceleration signal (wall motion), velocity (force of contraction/contractility) and displacement (stroke volume), and can further be processed to determine pre-ejection intervals, ejection time, and maximum rate of change of ventricular volume. Thus, one technique for estimating contractility based upon signals from an accelerometer within the right ventricle is as follows. The accelerometer generates signals representative of the speed at which the ventricular wall moves during a contraction. The increase in contractility caused by a sudden drop in ventricular filling results in the ventricular walls moving more forcefully. Hence, by monitoring the signals received from the accelerometer, controller 60 is able to estimate the contractility of the ventricle.

One specific technique for measuring heart contractility using an accelerometer is described within U.S. Pat. No. 5,480,412 to Mouchawar et al., entitled "System and Method for Deriving Hemodynamic Signals from a Cardiac Wall Motion Sensor," which is incorporated by reference herein.

Another technique for measuring heart contractility using an impedance sensor is described within U.S. Pat. No. 5,139,020 to Koestner, et al., entitled "Method and Apparatus for Controlling the Hemodynamic State of a Patient Based on Systolic Time Interval Measurements Detecting Using Doppler Ultrasound Techniques," which is incorporated by reference herein.

While the above patents demonstrate the existence of contractility sensors available, they are presented for illustration purposes and should not be considered a comprehensive list. The type of contractility sensor is not critical to the invention, and any sensor that provides an indicator of the strength of the contraction is considered within the scope of the invention.

Thus, controller 60 tracks the average and current contractility of the heart. The average contractility, stored within memory 94, is determined, for example, by averaging the measured contractility over relatively long periods of time such as minutes, hours, days, weeks, months or years. Controller 60 periodically compares the measured contractility with the average contractility and detects any sharp increase in contractility from one cardiac cycle to the next. As noted above, a sharp increase in contractility from one period to the next is indicative of the onset of vasovagal syncope, at least within patients subject to recurrent vasovagal syncope syndrome. If a sharp increase in contractility is detected, the controller promptly controls atrial and ventricular pulse generators 70 and 72 to increases the heart rate to compensate for the drop in blood pressure that initially triggered the increase in contractility.

Figure 3:
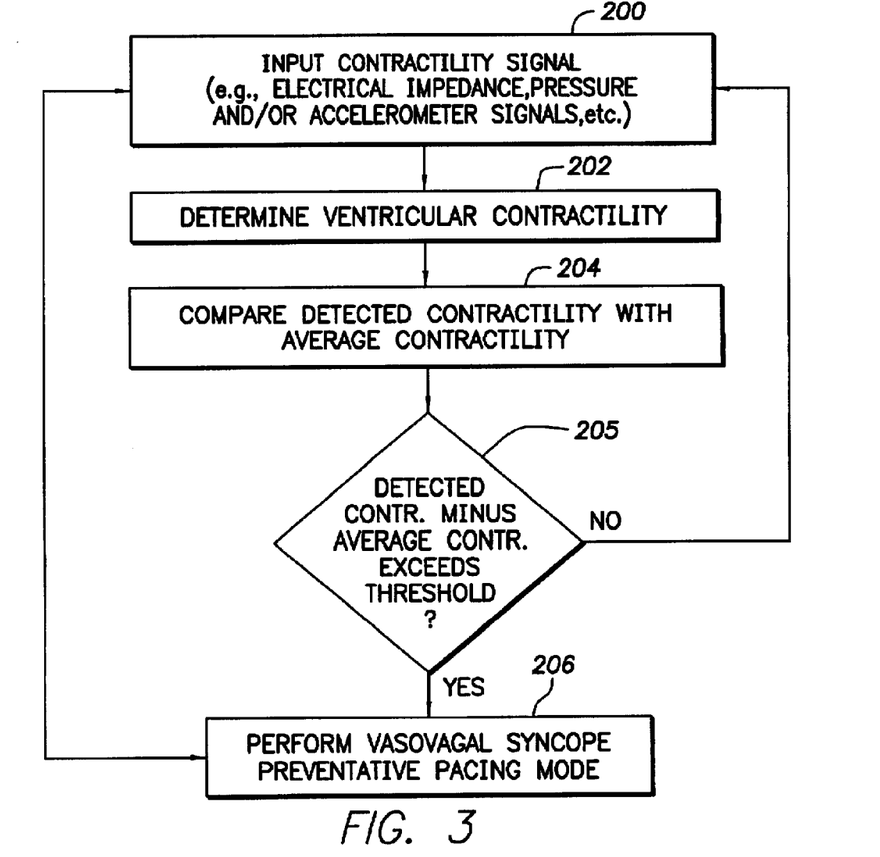
FIG. 3 is a flow chart illustrating steps performed by the pacemaker components of FIG. 2.

In FIG. 3, a flow chart is shown describing an overview of the operation of the novel features of the present invention. In this flow chart, and the other flow charts described herein, the various algorithmic steps are summarized in individual "blocks". Such blocks describe specific actions or decisions made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

Figure 2:
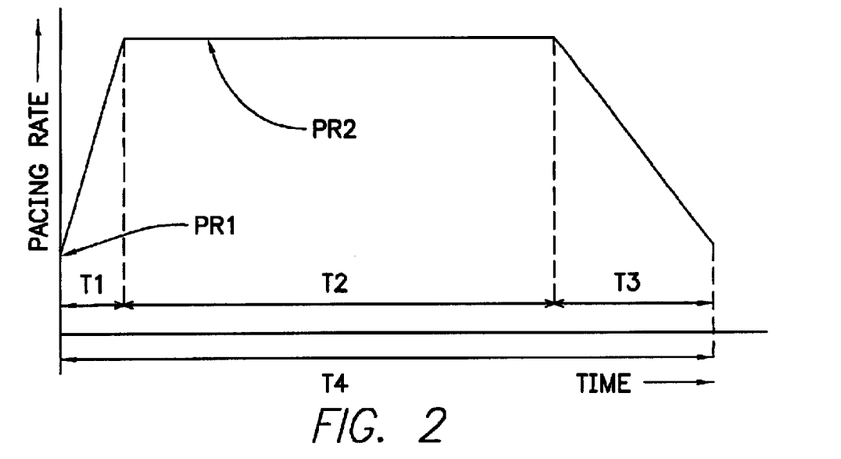
FIG. 2 is a graph illustrating a vasovagal syncope preventative pacing regime.

FIG. 2 illustrates a pacing regime which may be employed by controller 60 of FIG. 1 for prevention of vasovagal syncope. Upon detection of the sharp increase in contractility from one cardiac cycle to the next, the pacing rate is immediately increased from an initial pacing rate, PR1, (which may be a programmed base rate such as 60 bpm) to a syncope prevention rate, PR2 (which may be a programmable value, for example, 20, 30 or 40 bpm above the initial pacing rate, PR1). The increase from initial pacing rate, PR1, to syncope prevention rate, PR2, could be a linear increase performed during time T1 which may be, for example, in the range of three to five seconds. The heart is then continuously paced at syncope prevention rate, PR2, for time T2 which may be, for example, in the range of 30 seconds to 3 minutes (e.g., a predetermined or programmable interval). Then, the pacing rate is reduced from syncope prevention rate, PR2, to initial pacing rate, PR1, during T3, wherein T3 is, for example, in the range of 10 to 30 seconds (e.g., a predetermined or programmable interval).

In the alternative, each individual time value T1, T2 and T3 is not separately programmable. Rather, the overall time period T4 is programmed, and the pacemaker automatically calculates the subportions T1, T2 and T3 in accordance with prestored timing ratios. For ease of implementation T1, T2, T3 and T4 could be replaced with the number of the corresponding beats.

In yet another embodiment, the syncope prevention rate, PR2, and time T2 may be determined based on a measured contractility signal in the "normal" range, near the long-term average, for the patient. Contractility has been used in rate responsive pacemakers in a closed-loop fashion. See for example, U.S. Pat. No. 4,759,366 (Callaghan), which has already been incorporated herein by reference above. It is believed that contractility can likewise be used in a closed-loop fashion for vasovagal preventataive pacing.

By increasing the heart rate to syncope prevention rate, PR2, the drop in blood pressure that would otherwise occur during the onset of vasovagal syncope syndrome is at least partially compensated. Although the increase in the heart rate may not be sufficient to prevent the blood pressure from dropping to the point where the patient feels lightheaded or dizzy, it is typically sufficient to prevent the blood pressure from dropping to the point wherein the patient becomes unconscious. Even if the patient ultimately becomes unconscious, the loss of consciousness is delayed by at least some amount permitting the patient to take whatever action is necessary to ensure his or her safety. For example, if the patient is driving a vehicle, the patient, upon becoming lightheaded and dizzy, will preferably pull the vehicle to the side of the road. Thus, even if the patient loses consciousness, the delay in loss of consciousness may be sufficient to save the patient from injury.

By triggering the increase in pacing rate based upon a contractility measurement, the increase is triggered much more promptly than typically occurs within pacemakers configured to detect the onset of vasovagal syncope based upon bradycardia. As noted above, by the time a pacemaker has detected bradycardia, the blood pressure of the patient may already have dropped to the point where a subsequent increase in the heart rate is ineffective for preventing immediate loss of consciousness. By triggering the increase in heart rate based upon a sharp change in contractility, the increase is typically triggered within one or two beats subsequent to the initial drop in blood pressure, which marks the onset of vasovagal syncope. By significantly increasing the heart rate before the blood pressure has a chance to drop significantly, the pacemaker thereby either prevents any drop in blood pressure or, at the very least, defers the drop in blood pressure thereby delaying or preventing unconsciousness.

The steps performed by the components of FIG. 1 for vasovagal detection and prevention are summarized in FIG. 3. Briefly, at step 200, device 10 inputs or otherwise receives a signal from the contractility sensor 121 (e.g., the electrical impedance signals, pressure, accelerometer signals, ventricular gradient (PDI), PEP, heart sounds, etc.).

At step 202, device 10 determines the contractility and, at step 204, compares the detected contractility with the average contractility (e.g. a running average over at least the previous minutes, hours, day, etc.). If, at step 205, the contractility increases to the point where the detected contractility minus the average contractility exceeds a predetermined threshold, then step 206 is performed wherein the device 10 immediately increases the pacing rate to the vasovagal syncope preventative pacing mode using the pacing rate defined in FIG. 2. Otherwise, processing returns to step 200 wherein device 10 continues to monitor the contractility sensor 121 (e.g. the input impedance, pressure, accelerometer signals ventricular gradient (PDI), PEP, heart sounds, etc.). Vasovagal syncope preventative pacing mode performed at step 206 is administered, as described in connection with FIG. 2, for example, for about 30 seconds to 3 minutes. Then, the heart rate is reduced to a base pacing rate or pacing is eliminated completely. Ultimately, processing returns to step 100 to monitor impedance, accelerometer signals and/or pressure.

Thus, FIG. 3 illustrates, at a high level, steps performed to predict and prevent vasovagal syncope using device 10. As described above, device 10 additionally performs numerous other functions simultaneously, such as monitoring the heart to detect heart arrhythmias, such as atrial tachycardia. If a significant heart arrhythmia is detected while the pacemaker is administering the vasovagal syncope preventative pacing mode, the preventative pacing is terminated and the pacemaker administers whatever therapy is appropriate for the arrhythmia. The therapy may include the administration of defibrillation pulses or the like.

Figure 4:
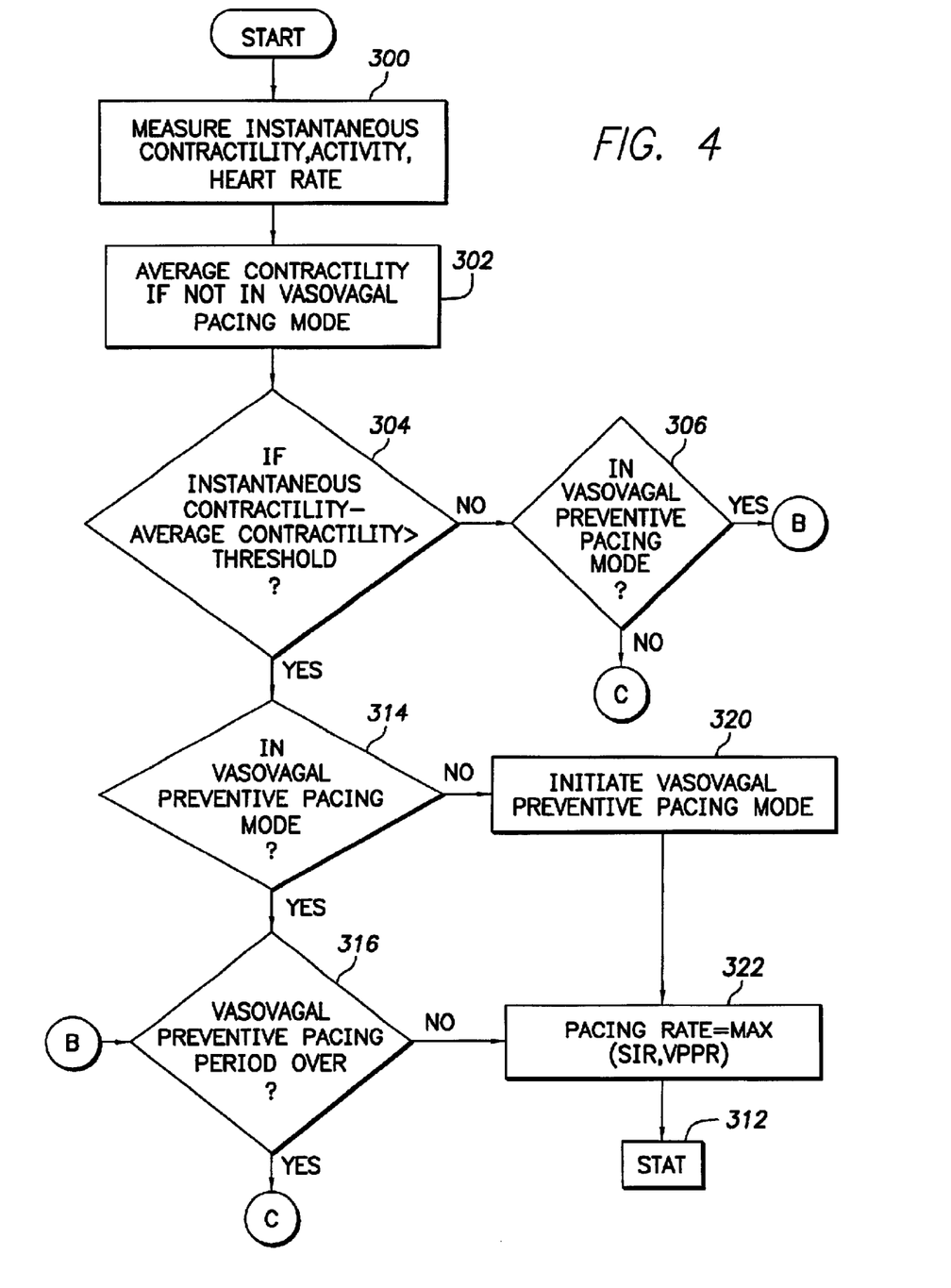
FIGS. 4–5 illustrate a detailed flow chart describing the steps performed by a pacemaker configured to pace the heart using a sensor indicated rate (SIR) and also configured to perform vasovagal syncope preventative pacing.
Figure 5:
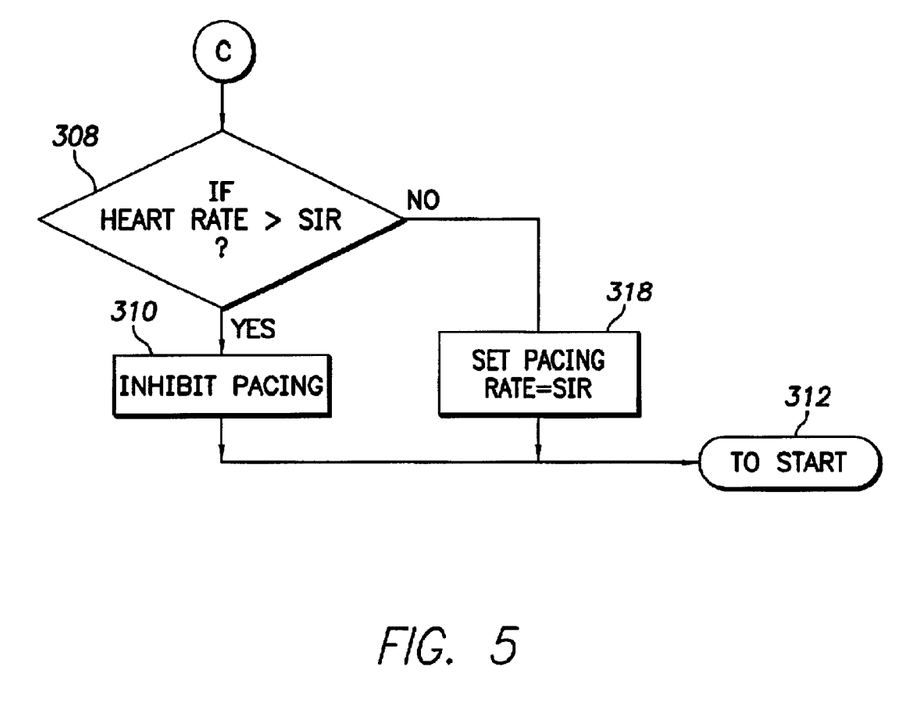

FIGS. 4 and 5 illustrate a sequence of steps performed to provide vasovagal preventative pacing within device 10 if the device is configured to pace at a sensor indicated rate (SIR). SIR pacing is described in further detail in U.S. Pat. No. 5,476,483 to Bornzin et al., entitled "System and Method for Modulating the Base Rate During Sleep for a Rate-Responsive Cardiac Pacemaker," which is incorporated by reference herein.

The sequence of steps illustrated in FIGS. 4 and 5 are generally in accordance with the techniques described above. Hence, the sequence of steps of FIGS. 4 and 5 will not be described in detail but merely summarized herein. Steps 300, 302, 304, 314, 320, 322 and 312 are steps performed by device 10 in response to the initial detection of a sharp increase in contractility wherein the vasovagal preventative pacing mode is initiated. Here, the patient is paced at either the vasovagal preventative pacing rate (VPPR) illustrated in FIG. 2 or a predetermined SIR, whichever is greater. If a further increase in contractility is detected while the patient is already within the vasovagal preventative pacing mode, the pacemaker continues to pace at either SIR or VPPR, whichever is greater. This is illustrated by steps 300, 302, 304, 314, 316, 322 and 312. Note that the vasovagal preventative pacing mode will be reinitiated so long as the contractility remains far above the average contractility level (step 304), i.e., the detected contractility minus the average contractility exceeds the predetermined threshold. In this regard, if the period for vasovagal preventative pacing has completed (step 216), VPPR pacing is suspended only as long as needed to detect that the contractility is still high and, during a subsequent execution of the steps of FIG. 4, VPPR pacing is again triggered.

Once contractility has dropped to an acceptable level, the pacemaker takes the patient out of the vasovagal preventative pacing mode. This is provided by steps 300, 302, 304, 306, 316, 308, 310 and 312 and also by steps 300, 302, 304, 306, 316, 308, 318 and 312.

What have been described are techniques for predicting and preventing vasovagal syncope within patients subject to recurrent vasovagal syncope using an implanted cardiac pacing device. Principles of the invention are applicable to predicting and preventing other types of syncope as well such as other types of neurocardiogenic syncope. Other physiological sensors that reflect the contractility change of the heart can be employed, such as ventricular gradient (also known as paced depolarization interval (PDI); pre-ejection period (PEP), etc.). The techniques are also applicable for use with other implantable medical devices, such as ICDs or the like. Thus, the specific examples herein are be illustrative of the invention and should not be g the scope of the invention.

What is claimed is:

1. In an implantable device, a system comprising:
    a pulse generator that generates stimulation pulses;
    a sensor that senses a parameter corresponding to contractility of a patient's heart and that generates corresponding signals; and
    a controller, coupled to the sensor and the pulse generator, that processes the signals from the sensor over time to determine an average contractility value and a current contractility value, and wherein the controller is responsive to the current contractility value differing from the average value by at least a predetermined amount to trigger the pulse generator to generate stimulation pulses according to a preventative mode, and wherein the preventative mode excludes drug infusion therapy.

2. The system of claim 1, wherein the sensor comprises a ventricular sensor that senses a signal representative of the contractility of at least one of the patient's ventricles.

3. The system of claim 1, wherein the sensor comprises an atrial sensor that senses a signal representative of the contractility of at least one of the patient's atria.

4. The system of claim 1, wherein the sensor comprises an impedance sensor that senses at least one of blood impedance, stroke volume, and a change in blood impedance of the patent's heart.

5. The system of claim 1, wherein the sensor comprises a motion sensor that detects at least one of heart wall acceleration, velocity, and displacement.

6. The system of claim 1, wherein the sensor comprises a blood pressure sensor.

7. The system of claim 1, wherein the sensor senses the patient's intracardiac electrogram signal.

8. The system of claim 7, wherein the sensor further comprises processing circuitry that integrates a portion of the intracardiac electrogram signal corresponding to a depolarization signal following a stimulation pulse.

9. The system of claim 7, wherein the sensor further comprises processing circuitry that is configured to measure the QT interval.

10. The system of claim 7, wherein the sensor further comprises processing circuitry that is configured to measure pre-ejection period.

11. The system of claim 1, wherein:
    the controller adjusts a rate of the stimulation pulses according to a predetermined transfer curve.

12. In an implantable device, a system comprising:
    a pulse generator that generates stimulation pulses;
    a sensor that senses a parameter corresponding to contractility of a patient's heart and that generates corresponding signals; and
    a controller, coupled to the sensor and the pulse generator, that processes the signals from the sensor over time to determine an average contractility value and a current contractility value, and wherein the controller is responsive to the current contractility value differing from the average value by at least a predetermined amount to trigger the pulse generator to generate stimulation pulses according to a preventataive mode;
    wherein the controller adjusts a rate of the stimulation pulses according to a predetermined transfer curve; and
    wherein the predetermined transfer curve comprises an incremental increase from a preexisting pacing rate to a predetermined high rate during a first predetermined number of beats, a predetermined high rate during a second predetermined of number of beats, and an incremental decrease in the pacing rate from the predetermined high rate to the preexisting pacing rate during a third predetermined of number of beats.

13. The system of claim 12, wherein the first, second and third predetermined number of beats correspond to a range of 3 to 5 seconds, 30 to 180 seconds, and 10 to 30 seconds, respectively.

14. The system of claim 12, wherein the predetermined high rate is in the range of 20 to 40 beats per minute above the preexisting pacing rate.

15. The system of claim 12, wherein the preexisting pacing rate is a predetermined base pacing rate.

16. The system of claim 12, wherein the preexisting pacing rate is a sensor responsive pacing rate.

17. The system of claim 12, wherein:
    the controller determines the predetermined high rate based on the sensed contractility.

18. The system of claim 17, wherein:
    the controller dynamically adjusts the predetermined high rate in a closed-loop fashion based on the sensed contractility.

19. In an implantable device, a method for treating vasovagal syncope within a patient, the method comprising:
    sensing a parameter corresponding to contractility of the patient's heart and generating corresponding signals over time;
    processing the signals to determine an average contractility value and a current contractility value; and
    generating stimulation pulses at a predetermined rate to overdrive the patient's heart rate when the current contractility value differs from the average contractility value by at least a predetermined amount;
    wherein the patient's heart is overdriven without drug infusion therapy.

20. The method of claim 19, wherein generating comprises:
    generating stimulation pulses preemptively before the occurrence of a sudden rate drop associated with vasovagal syncope.

21. The method of claim 19, further comprising determining that there is a significant risk of the onset of vasovagal syncope based upon the current value of the contractility being greater than a predetermined amount from the average contractility value.

22. The method of claim 19, wherein sensing comprises: sensing a signal representative of the contractility of at least one of the patent's ventricles.

23. The method of claim 19, wherein sensing comprises: sensing a signal representative of the contractility of at least one of the patient's atria.

24. The method of claim 19, wherein sensing comprises: sensing an impedance signal in the patient's heart; and processing the impedance signal to produce at least one of blood impedance, stroke volume, and a change in blood impedance of the patents heart to determine the force of contraction.

25. The method of claim 19, wherein sensing comprises: detecting cardiac wall motion signal; and processing the cardiac wall motion signal to produce at least one of heart wall acceleration, velocity and displacement of the patients heart to determine the force of contraction.

26. The method of claim 19, wherein sensing comprises: sensing a parameter corresponding to the patient's blood pressure and generating a corresponding signal; and processing the signal to determine the force of contraction.

27. The method of claim 19, wherein sensing comprises: sensing electrogram signals of the patients heart; and processing the electrogram signal to determine the force of contraction.

28. The method of claim 27, wherein processing the electrogram further comprises:
integrating a depolarization signal that follows a stimulation pulse.

29. The method of claim 27, wherein processing the electrogram further comprises measuring a QT interval.

30. The method of claim 27, wherein processing the electrogram further comprises measuring a pre-ejection period.

31. The method of claim 19, wherein generating comprises:
determining a vasovagal rate based on the sensed contractility signal; and
adjusting from a preexisting rate to the vasovagal rate.

32. In an implantable device, a method for treating vasovagal syncope within a patient, the method comprising:
sensing a parameter corresponding to contractility of the patient's heart and generating corresponding signals over time;
processing the signals to determine an average contractility value and a current contractility value; and
generating stimulation pulses at a predetermined rate to overdrive the patient's heart rate when the current contractility value differs from the average contractility value by at least a predetermined amount;
wherein generating comprises:
incrementally increasing from a preexisting pacing rate to a predetermined high rate;
maintaining a predetermined high rate for a first predetermined amount of time; and
incrementally decreasing the predetermined high rate to the preexisting pacing rate during a second predetermined amount of time.

33. In an implantable device, a method for treating vasovagal syncope within a patient, the method comprising sensing a parameter corresponding to contractility of the patient's heart and generating corresponding signals over time;
processing the signals to determine an average contractility value and a current contractility value; and
generating stimulation pulses at a predetermined rate to overdrive the patient's heart rate when the current contractility value differs from the average contractility value by at least a predetermined amount;
wherein generating comprises:
incrementally increasing from a preexisting pacing rate to a predetermined high rate during a first predetermined on number of beats;
maintaining a predetermined high rate during a second predetermined on number of beats; and
incrementally decreasing from the predetermined high rate to the preexisting pacing rate during a third predetermined on number of beats.

34. In an implantable device, a system for treating vasovagal syncope within a patient the system comprising:
pulse generating means for generating stimulation pulses;
physiological sensing means for sensing a parameter corresponding to contractility of the patient's heart;
means for determining an average contractility value and a current contractility value;
means for determining if the current contractility value differs from the average contractility value by at least a predetermined amount; and
means for triggering the pulse generating means to generate stimulation pulses at a predetermined rate so as to overdrive the intrinsic heart rate;
wherein the intrinsic heart rate is overdriven without drug infusion therapy.

35. The system of claim 34, wherein the physiological sensing means comprises:
means for sensing a signal representative of the contractility of at least one of the patient's ventricles.

36. The system of claim 34, wherein the physiological sensing means comprises:
means for sensing a signal representative of the contractility of at least one of the patient's atria.

37. The system of claim 34, herein the physiological sensing means comprises:
impedance measuring means for measuring an impedance corresponding to at least one of blood impedance, stroke volume and a change in blood impedance of the patients heart.

38. The system of claim 34, wherein the physiological sensing means comprises:
motion detecting means for detecting cardiac wall motion corresponding to at least one of heart wall acceleration, velocity and displacement.

39. The system of claim 34, wherein the physiological sensing means comprises means for sensing blood pressure.

40. The system of claim 34, wherein the physiological sensing means comprises electrogram sensing means for sensing intracardiac electrogram signals of the patient's heart.

41. The system of claim 40, wherein the electrogram sensing means comprises means for integrating the depolarization portion of the electrogram.

42. The system of claim 40, wherein the electrogram sensing means comprises means for determining the QT interval.

43. The system of claim 40, wherein the electrogram sensing means comprises means for determining pre-ejection period.

44. The system of claim 40, wherein the means for triggering comprises:

means for adjusting a current pacing rate to a predetermined high rate;

means for providing stimulation pulses at a predetermined high rate for a first predetermined time period; and means for adjusting the predetermined high rate to a base rate for a second predetermined time period.

45. The system of claim 34, wherein the means for triggering comprises:

means for adjusting a current pacing rate to a rate that reduces the contractility signal to the average value.

46. In an implantable device, a system comprising:

a pulse generator that generates stimulation pulses;

a cardiac impedance sensor that senses cardiac impedance values and generates corresponding signals; and a controller, coupled to the cardiac impedance sensor and the pulse generator, that processes the signals from the cardiac impedance sensor to determine whether there is a risk of an onset of vasovagal syncope, and that triggers the pulse generator to generate stimulation pulses at a predetermined rate if the risk exists;

wherein the stimulation pulses at the predetermined rate are generated without infusion of a drug.

47. The system of claim 46, wherein the sensor comprises a ventricular sensor that senses a signal representative of the contractility of at least one of the patient's ventricles.

48. The system of claim 46, wherein the sensor comprises an atrial sensor that senses a signal representative of the contractility of at least one of the patient's atria.

49. The system of claim 46, wherein the controller is operative to trigger the pulse generator to generate stimulation pulses at an overdrive pacing rate.

50. In an implantable device, a method for treating vasovagal syncope within a patient, the method comprising;

sensing cardiac impedance values of the patient's heart and generating corresponding signals over time;

processing the signals to determine whether there is a risk of an onset of vasovagal syncope; and generating stimulation pulses at a predetermined rate if the risk exists;

wherein the stimulation pulses at the predetermined rate are generated without infusion of a drug.

\* \* \* \* \*